(12) United States Patent
Miyata et al.

(10) Patent No.: US 9,815,000 B2
(45) Date of Patent: Nov. 14, 2017

(54) N-METHYL-2-PYRROLIDONE DISTILLING APPARATUS

(71) Applicant: MITSUBISHI CHEMICAL ENGINEERING CORPORATION, Tokyo (JP)

(72) Inventors: Kenyo Miyata, Tokyo (JP); Tomoyuki Kawada, Tokyo (JP); Katsuhiro Katou, Tokyo (JP)

(73) Assignee: MITSUBISHI CHEMICAL ENGINEERING CORPORATION, Tokyo (JP)

( * ) Notice: Subject to any disclaimer, the term of this patent is extended or adjusted under 35 U.S.C. 154(b) by 252 days.

(21) Appl. No.: 14/837,434

(22) Filed: Aug. 27, 2015

(65) Prior Publication Data

US 2015/0367249 A1    Dec. 24, 2015

Related U.S. Application Data

(62) Division of application No. 13/395,980, filed as application No. PCT/JP2010/065213 on Sep. 6, 2010, now abandoned.

(30) Foreign Application Priority Data

Sep. 14, 2009   (JP) .................................. 2009-212426

(51) Int. Cl.
   *C07D 207/267*   (2006.01)
   *B01D 3/42*       (2006.01)
   *B01D 3/14*       (2006.01)

(52) U.S. Cl.
   CPC ............ *B01D 3/4211* (2013.01); *B01D 3/143* (2013.01); *C07D 207/267* (2013.01)

(58) Field of Classification Search
   CPC ... B01D 3/4211; B01D 3/143; C07D 207/267
   See application file for complete search history.

(56) References Cited

U.S. PATENT DOCUMENTS 2,768,942 A    10/1956   Marple et al.
3,449,215 A    6/1969    Lupper et al.
(Continued)

FOREIGN PATENT DOCUMENTS

FR    1.133.563    3/1957
FR    2 656 305    6/1991
(Continued)

OTHER PUBLICATIONS

European Search Report in EP 10 81 5325 dated Feb. 18, 2014.
(Continued)

*Primary Examiner* — In Suk Bullock
*Assistant Examiner* — Youngsul Jeong
(74) *Attorney, Agent, or Firm* — Nixon & Vanderhye P.C.

(57) ABSTRACT

A distillation apparatus for NMP including a first distillation column in which the spent NMP as a liquid to be treated is subjected to distillation; and a second distillation column in which bottoms from the first distillation column are further subjected to distillation, the distillation apparatus being provided with an automatic treatment function including a start-up function, and then a continuous treatment operation of the distillation apparatus being initiated; and an operational mode switching function in which upon the continuous treatment operation, an operational mode of the distillation apparatus being switched again to the circulation operation according to a level of the liquid in the raw material tank or a level of the liquid in the product tank.

11 Claims, 1 Drawing Sheet

(56) References Cited

U.S. PATENT DOCUMENTS

| | | | |
|---|---|---|---|
| 3,642,614 A | 2/1972 | Van Tassell | |
| 4,501,902 A | 2/1985 | Cleary | |
| 4,976,825 A | 12/1990 | Iwasaki et al. | |
| 5,021,128 A * | 6/1991 | Palmer | B01D 3/02 137/392 |
| 5,207,874 A | 5/1993 | Hess et al. | |
| 5,763,712 A | 6/1998 | Roth et al. | |
| 7,037,412 B2 | 5/2006 | Abe et al. | |
| 2002/0139657 A1 | 10/2002 | Ugamura et al. | |
| 2007/0256920 A1 | 11/2007 | Kanauchi et al. | |
| 2010/0243423 A1 | 9/2010 | Ogawa et al. | |

FOREIGN PATENT DOCUMENTS

| | | | |
|---|---|---|---|
| JP | 6-263725 | 9/1994 | |
| JP | 6-279401 | 10/1994 | |
| JP | 8-27105 | 1/1996 | |
| JP | 8-109167 | 4/1996 | |
| JP | H08109167 A * | 4/1996 | ......... C07D 207/267 |
| JP | 2007-269638 | 10/2007 | |
| WO | WO 2009/069584 | 6/2009 | |

OTHER PUBLICATIONS

International Preliminary Report on Patentability issued in PCT/JP2010/065213 dated Apr. 19, 2015.

International Search Report for PCT/JP2010/65213 dated Oct. 26, 2010.

* cited by examiner

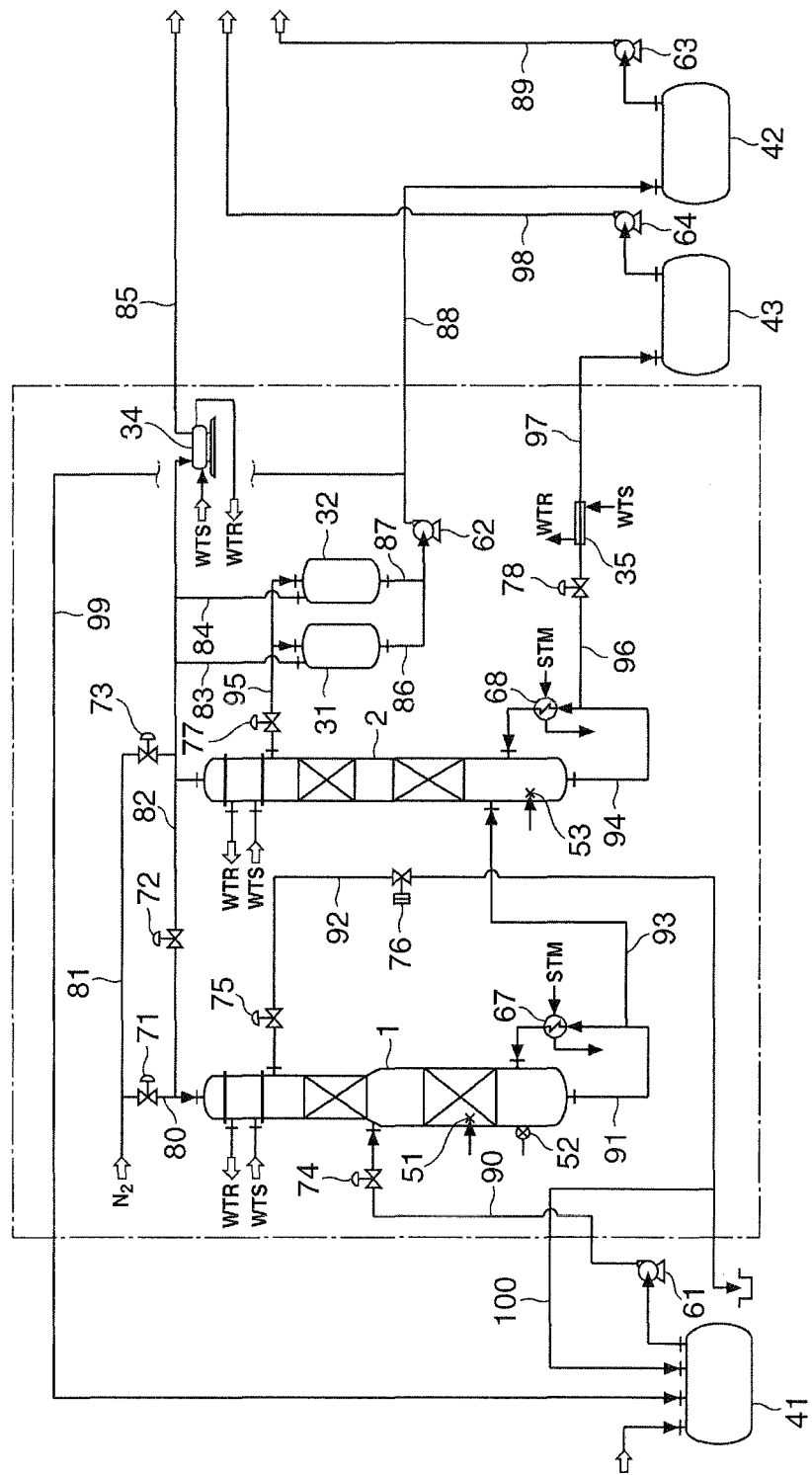

N-METHYL-2-PYRROLIDONE DISTILLING APPARATUS

This application is a divisional of U.S. application Ser. No. 13/395,980, filed May 22, 2012, which is the U.S. national phase of International Application No. PCT/JP2010/065213 filed Sep. 6, 2012 which designated the U.S. and claims priority to JP 2009-212426 filed Sep. 14, 2009, the entire contents of each of which are hereby incorporated by reference.

TECHNICAL FIELD

The present invention relates to a distillation apparatus for NMP, and more particularly, to a distillation apparatus for NMP which is capable of purifying a spent NMP (N-methyl-2-pyrrolidone) recovered from a step for producing electrodes for lithium ion secondary batteries, etc., on-site for recycling the NMP.

BACKGROUND ART

Upon production of lithium ion secondary batteries, a base material is coated with an electrode material comprising an active substance such as a lithium compound, a binder such as polyvinylidene fluoride, and N-methyl-2-pyrrolidone (hereinafter referred to merely as "NMP") as a solvent, and the resulting coated material is calcined to produce an electrode. The NMP generated in a gaseous state in the calcination step is recovered by an adsorption method or a water-absorbing method to thereby previously prepare an aqueous solution comprising the NMP at a concentration of not more than 80% in view of the problem of safety upon transportation. Thereafter, the thus prepared aqueous NMP solution is transported to chemical plants to purify the recovered NMP again into a high-purity NMP product. Meanwhile, in the chemical plants, the recovered NMP is purified by known distillation methods to obtain the purified NMP having a purity of not less than 99.9% which is similar to a purity of NMP initially produced.

PRIOR DOCUMENTS

Patent Documents

Patent Document 1: Japanese Patent Application Laid-Open (KOKAI) No. 6-279401
Patent Document 2: Japanese Patent Application Laid-Open (KOKAI) No. 6-263725
Patent Document 3: Japanese Patent Application Laid-Open (KOKAI) No. 8-27105

SUMMARY OF THE INVENTION

Problems to be Solved by the Invention

By the way, upon recycling the NMP, not only transportation costs but also a pretreatment for controlling a concentration thereof, etc., are required, as described above. Therefore, upon production of the above batteries, etc., it is desired to purify the NMP on-site from the viewpoint of reducing burdens thereon. However, in order to accomplish distillative purification of the NMP, highly skilled techniques are needed. For this reason, it will be practically difficult to suitably perform the distillative purification process in other places than the chemical plants. More specifically, the NMP recovered from the production process of the batteries comprises low-boiling components having a boiling point being intermediate between boiling points of water and the NMP and high-boiling components derived from the NMP. Therefore, in order to purify the NMP, it is required to conduct a precise two-stage distillation process. In addition, there tends to arise such a problem that a stationary operation of the distillation apparatus is difficult because the water content in the NMP (concentration of the NMP) is varied owing to seasonal variation or variation of the production process, and throughput is also varied therewith.

The present invention has been accomplished to solve the above problems. An object of the present invention is to provide a distillation apparatus for NMP for regenerating a spent NMP recovered from a step of producing an electrode for lithium ion batteries which is capable of purifying the NMP in a simple and safe manner irrespective of variation in concentration of water in the raw material or throughput, and is suitable for conducting an automatic operation thereof on-site.

Means for Solving the Problems

In the present invention, there is used a double column type distillation apparatus including a first distillation column in which water comprising low-boiling components is removed from a raw NMP to purify the raw NMP and obtain a high-concentration NMP; and a second distillation column in which high-boiling components are removed from the high-concentration NMP to purify the high-concentration NMP and obtain a high-purity NMP. The distillation apparatus is provided, as an automatic treatment function, with a start-up function in which a reduced pressure operation and a circulation operation are sequentially performed for controlling the respective distillation columns in a stationary state to initiate a continuous treatment operation of the distillation apparatus; and an operational mode switching function in which upon the continuous treatment operation, an operational mode of the distillation apparatus is switched again to the circulation operation according to a level of the liquid in a raw material tank or a product tank. As a result, the distillation apparatus can be operated in a simple and safe manner corresponding to the variation of throughput or water content in the raw material.

That is, in an aspect of the present invention, there is provided a distillation apparatus for NMP in which a spent NMP comprising low-boiling components and high-boiling components as impurities is purified, which distillation apparatus comprises:

a raw material tank for storing the spent NMP as a liquid to be treated;

a first distillation column in which the liquid to be treated which is supplied from the raw material tank is subjected to distillation and separated into a high-concentration NMP having a concentration of not less than 99% by weight and water comprising the low-boiling components as bottoms and a distillate, respectively;

a second distillation column in which the bottoms from the first distillation column are further subjected to distillation and separated into a high-purity NMP having a concentration of not less than 99.9% by weight and the high-concentration NMP comprising the high-boiling components as distillate and a bottoms, respectively; and a product tank for storing the high-purity NMP obtained as the distillate from the second distillation column, and which distillation apparatus is provided with an automatic treatment function comprising:

a start-up function in which after previously performing a reduced pressure operation of each of the first and second distillation columns, a circulation operation in which the liquid to be treated is fed from the raw material tank to the first distillation column and the distillate from the second distillation column is fed back to the raw material tank, is performed to control the respective distillation columns in a stationary state, and then a continuous treatment operation of the distillation apparatus is initiated; and an operational mode switching function in which upon the continuous treatment operation, an operational mode of the distillation apparatus is switched again to the circulation operation in the case where a level of the liquid in the raw material tank is lowered to a predetermined height during the continuous treatment operation or in the case where a level of the liquid in the product tank is raised to a predetermined height during the continuous treatment operation.

Effect of the Invention

The distillation apparatus according to the present invention comprises the first distillation column in which water comprising low-boiling components is removed from a raw NMP to obtain purified high-concentration NMP, and the second distillation column in which high-boiling components are further removed from the high-concentration NMP to obtain purified high-purity NMP. In addition, the distillation apparatus according to the present invention is provided with an automatic treatment function including a start-up function of successively performing a reduced pressure operation and a circulation operation in each of the first and second distillation columns to initiate a continuous treatment operation of the distillation apparatus, and an operational mode switching function of switching an operational mode of the distillation apparatus to the circulation operation during the continuous treatment operation of the distillation apparatus. Therefore, the NMP can be purified in a simple and safe manner on-site while conducting an automatic operation of the distillation apparatus without need of highly skilled techniques.

BRIEF DESCRIPTION OF THE DRAWING

The FIGURE is a flow diagram showing an example of a construction of a main portion of a distillation apparatus for NMP according to the present invention.

PREFERRED EMBODIMENTS FOR CARRYING OUT THE INVENTION

A preferred embodiment of the distillation apparatus for NMP according to the present invention (hereinafter referred to merely as a "distillation apparatus") is described below. The "NMP" as used in the present invention means N-methyl-2-pyrrolidone or an aqueous solution comprising N-methyl-2-pyrrolidone as a main component. In addition, examples of impurities contained in the spent NMP as a liquid to be treated (hereinafter referred to merely as a "raw NMP") includes low-boiling components whose boiling point lies between boiling points of water and NMP such as formic acid, and high-boiling components derived from NMP such as g-butyl lactone (GBL) and n-methyl succinimide.

The distillation apparatus according to the present invention is an automatically operable double column type apparatus for purifying the raw NMP comprising the low-boiling components and the high-boiling components as impurities.

As shown in FIG. 1, the distillation apparatus according to the present invention generally comprises a raw material tank 41 for storing the raw NMP as a liquid to be treated, a first distillation column 1 in which the liquid to be treated which is supplied from the raw material tank is subjected to distillation and separated into a high-concentration NMP having a concentration of not less than 99% by weight and water comprising the low-boiling components as bottoms and a distillate, respectively; a second distillation column 2 in which the bottoms from the first distillation column 1 are further subjected to distillation and separated into a high-purity NMP having a concentration of not less than 99.9% and the high-concentration NMP comprising high-boiling components as distillate and a bottoms, respectively; a first check drum 31 and a second check drum 32 in which the high-purity NMP obtained as the distillate from the second distillation column is temporarily recovered to sample a test specimen for analysis; a product tank 42 for storing the high-purity NMP recovered in these check drums; and a waste liquid tank 43 for storing the high-concentration NMP (waste liquid) comprising the high-boiling components which is obtained as the bottoms in the second distillation column.

The raw material tank 41 is a container for storing the raw NMP having, for example, a concentration of not more than 95% by weight, usually a concentration of about 70 to about 90% by weight which is discharged, for example, from a step of producing an electrode for lithium ion secondary batteries, and may be provided for conducting a distillation treatment in a continuous and efficient manner. To the raw material tank 41 are connected not only a flow path for delivering the raw NMP from the electrode production step to the raw material tank, but also a raw material feed flow path 90 for feeding the raw NMP as a liquid to be treated to the first distillation column 1. The reference numeral 61 denotes a raw material feed pump, and the reference numeral 74 denotes a flow control valve.

The first distillation column 1 and the second distillation column 2 are distillation columns in which the raw NMP fed is subjected distillative purification. The first distillation column 1 is provided for purifying the raw NMP and obtaining a high-concentration NMP from which the low-boiling components and water are removed, whereas the second distillation column 2 is provided for further purifying the high-concentration NMP and obtaining a high-purity NMP from which the high-boiling components are removed. The first distillation column 1 and the second distillation column 2 are constructed from conventionally known distillation columns, namely, a packing column an inside of which is packed with irregular packing materials or regular packing materials, a plate column in which a number of trays (plates) for gas-liquid contact such as porous plate trays are disposed, etc.

The first distillation column 1 is constructed such that the raw NMP to be treated is supplied to the respective plates in the column through the above flow path 90. The first distillation column 1 is equipped at a bottom portion thereof with a boiling mechanism including a reboiler 67 for heating and vaporizing the raw NMP. Such a boiling mechanism serves for boiling the raw NMP in a bottom portion of the first distillation column 1, and comprises the reboiler 67 for heating and vaporizing the raw NMP by heat exchange with a heat medium such as water vapor, and a flow path 91 for circulation of the bottoms through which the raw NMP is withdrawn from the bottom portion of the first distillation column 1 and fed to the reboiler 67, and the NMP vaporized in the reboiler is returned back to the bottom portion.

As the reboiler 67, there may be used a multi-pipe type heat exchanger in which a number of flow paths are constructed by a plurality of heat transfer pipes. On an upstream side of the reboiler 67 in the flow path 91, there is provided a flow path 93 which is branched from the flow path 91 for feeding a part of the bottom liquid circulated in the bottom portion of the first distillation column 1, i.e., for feeding the high-concentration NMP concentrated in the first distillation column 1 as the bottoms to the second distillation column 2.

The first distillation column 1 is also provided at a top portion thereof with a condenser for condensing water vapor separated from the raw NMP. As the condenser, there may be usually used those condensers of a multi-pipe type, a spiral type, a plate type, a double tube type, etc., in which a cooling medium is flowed through a plurality of heat transfer tubes or heat transfer plates constituting a number of flow paths, and condensable water vapor (water vapor separated by distillation) is passed therethrough for liquefaction thereof. The cooling condenser is provided at a bottom thereof with a flow path 92 through which condensed water as a distillate comprising the low-boiling components as impurities is discharged out of the system. On the flow path 92, there are disposed a flow control valve 75 and a drain valve 76 for controlling an amount of the distillate discharged. Further, branched from the flow path 92 is a flow path 100 for feeding the distillate of the first distillation column 1 back to the raw material tank 41 upon the below-mentioned circulation operation. In addition, the first distillation column 1 is connected at a top thereof with the below-mentioned flow path 80 for reducing a pressure within the first distillation column 1 and feeding an inert gas thereto.

On the other hand, the second distillation column 2 is constructed such that the high-concentration NMP distilled and separated in the first distillation column 1 is fed to a bottom portion of the second distillation column through the above flow path 93. The second distillation column 2 is provided at the bottom portion thereof with a boiling mechanism including a reboiler 68 for further heating and vaporizing the high-concentration NMP. Such a boiling mechanism is the same boiling mechanism as provided in the first distillation column 1, and comprises the reboiler 68 for heating and vaporizing the high-concentration NMP, and a flow path 94 for circulation of a bottom liquid through which the high-concentration NMP is withdrawn from the bottom portion of the second distillation column 2 and fed to the reboiler 68, and the NMP vaporized in the reboiler is fed back to the bottom portion of the second distillation column.

The reboiler 68 used above may be the same as the above reboiler 67. On an upstream side of the reboiler 68, there is provided a flow path 96 which is branched from the flow path 94 for feeding a part of the high-concentration NMP circulated in the bottom portion of the second distillation column 2, i.e., for withdrawing a bottom liquid remaining in the second distillation column 2 and comprising high-boiling component as impurities, as the bottoms thereof. On a downstream side of the flow path 96, there are disposed a waste liquid cooler 35 for cooling the thus withdrawn high-concentration NMP, a flow path 97 for delivering the thus cooled high-concentration NMP to a waste liquid tank 43, and a flow path 98 for appropriately withdrawing the high-concentration NMP as a waste liquid temporarily stored in the waste liquid tank 43 out of the system. Meanwhile, the reference numeral 78 denotes a flow control valve for controlling a flow rate of the bottoms, and the reference numeral 64 denotes a pump for discharging the waste liquid.

The second distillation column 2 is also provided at a top thereof with a condenser for condensing the high-purity NMP thus separated. As such a condenser, there may be used the same condensers as used in the above first distillation column 1. The above condenser is provided at a bottom thereof with a flow path 95 through which the condensed high-purity NMP is withdrawn as a distillate. The flow path 95 is connected to a first check drum 31 and a second check drum 32. The reference numeral 77 denotes a flow control valve for controlling a flow rate of the distillate. The above first check drum 31 and second check drum 32 are provided for analyzing a purity of the high-purity NMP obtained in the second distillation column 2 and judging whether or not the high-purity NMP is acceptable as a final product. Although not shown in FIG. 1, a changeover valve may be disposed on the flow path 95 between the first check drum 31 and the second check drum 32 for alternately receiving the high-purity NMP in the first check drum 31 and the second check drum 32.

Meanwhile, the second distillation column 2 is connected at a top thereof with the below-mentioned flow path 82 for reducing a pressure within the second distillation column 2 and feeding an inert gas thereto. In addition, the first check drum 31 and the second check drum 32 are connected with the below-mentioned flow paths 83 and 84, respectively, for reducing a pressure within the respective containers and feeding an inert gas thereto.

Also, in order to withdraw the purified high-purity NMP, the first check drum 31 is connected with a flow path 86, and the second check drum 32 is connected with a flow path 87. These flow paths 86 and 87 are connected to the product tank 42 through a product withdrawal pump 62 and a flow path 88. Although not shown in FIG. 1, the flow path 86 and the flow path 87 are respectively provided thereon with a switching valve for delivering the high-purity NMP from either one of the first check drum 31 and the second check drum 32 to the product tank 42 in a switching manner. In addition, there is provided a flow path 99 which is branched from the flow path 88 and serves for feeding the high-purity NMP distilled off from the second distillation column 2 and stored in either one of the first check drum 31 and the second check drum 32 back to the raw material tank 41 upon the below-mentioned circulation operation. The product tank 42 is a container for storing the high-purity NMP and may be constructed such that the high-purity NMP is fed, for example, to the battery production process through a product feed pump 63 and a flow path 89, if necessary.

In the distillation apparatus according to the present invention, in order to conduct the distillation procedure under reduced pressure similarly to an ordinary distillation procedure, there may also be additionally provided a reduced pressure line for evacuating the system. In addition, in order to prevent inclusion of oxygen and control a pressure within the system, there may also be additionally provided an inert gas line for feeding a nitrogen gas into the system.

More specifically, the first distillation column 1 is connected at a top thereof with a flow path 80 which extends from a nitrogen gas feed facility and is provided thereon with a pressure regulating valve 71. The second distillation column 2 is connected at a top thereof with a flow path 82 which is branched from the above flow path 80 on a downstream side of the pressure regulating valve 71 and provided thereon with a pressure regulating valve 72. The flow path 82 is branched at a top portion of the second distillation column 2, and further the above flow paths 83 and 84 are branched from the flow path 82 and connected to the first check drum 31 and the second check drum 32, respectively. Further, the flow path 82 is coupled at a tip end thereof to a vacuum pump 34 for evaluating an inside of the system. A flow path 85 is a flow path for discharge from the vacuum pump 34. In addition, on an upstream side of the pressure regulating valve 71 on the flow path 80 for feeding nitrogen, there is provided a flow path 81 which is branched from the flow path 80 for feeding nitrogen to the second distillation column 2, the first check drum 31 and the second check drum 32. The flow path 81 is provided thereon with a pressure regulating valve 73, and coupled at a tip end thereof with the above flow path 82 on a downstream side of the pressure regulating valve 72.

In the distillation apparatus according to the present invention, in order to control a distillation procedure in the first distillation column 1 and the second distillation column 2 to thereby execute the below-mentioned automatic treatment function, the first distillation column 1 is provided, for example in a lower packing layer on a bottom side thereof, with a thermometer 51, and further the first distillation column 1 is provided at a bottom portion thereof with a level meter 52. Also, the second distillation column 2 is provided at a bottom portion thereof with a thermometer 53 and a level meter (not shown). Using a control device loaded with a distillation program, operation of the boiling mechanism, opening and closing of the respective flow paths, switching therebetween, flow rate control therethrough, etc., are performed on the basis of preset treatment conditions, the above temperatures, detection signals from detectors disposed at a level of the liquid, etc.

The distillation apparatus according to the present invention is constructed so as to execute an automatic treatment function to be accomplished by the above control device which includes a start-up function in which a reduced pressure operation and a circulation operation are sequentially performed to control the respective distillation columns in a stationary state, and then a continuous treatment operation of the distillation apparatus is initiated; an operational mode switching function in which an operational mode of the distillation apparatus is switched from the continuous treatment operation to the circulation operation, and an automatic stopping function. In the followings, the operating method of the distillation apparatus according to the present invention, the method for purifying the NMP and the above automatic treatment function are explained.

[Reduced Pressure Operation]

According to manipulation of a control panel for initiating an operation of the distillation apparatus, first, in order to perform the reduced pressure operation, the vacuum pump 34 is actuated to reduce an inside pressure of each of the first distillation column 1 and the second distillation column 2 as well as the first check drum 31 and the second check drum 32 to a predetermined value through the flow paths 80, 82, 83 and 84. In this case, the inside pressure of the system is once evacuated until reaching 100 Torr or less, and then a trace amount of nitrogen is fed from the nitrogen gas feed facility to the first distillation column 1 and the second distillation column 2 as well as the first check drum 31 and the second check drum 32 through the flow paths 80 and 81 to maintain the pressures within these devices at a constant value.

Upon the above reduced pressure operation, in order to prevent production of by-products owing to increase in inside temperatures of the respective devices, for example, the pressure within the first distillation column 1 is set to 100 Torr by controlling the pressure regulating valves 71 and 72, and the pressures within the second distillation column 2 as well as the first check drum 31 and the second check drum 32 are set to 100 Torr or less by controlling the pressure regulating valve 73. Meanwhile, although the first distillation column 1 is held under a more reduced pressure than that of the second distillation column 2, it is possible to operate the distillation apparatus using the vacuum pump 34 singly by controlling an amount of a gas absorbed in the first distillation column 1 through the pressure regulating valve 72.

[Circulation Operation]

After conducting the reduced pressure operation, it should be avoided to immediately perform a distillation treatment, and a total reflux operation using a make-up solution previously stored in the first distillation column 1 and the second distillation column 2 is performed to stabilize the system. With the total reflux operation, the first distillation column 1 and the second distillation column 2 are respectively controlled in a stationary state, so that the distillation apparatus can be smoothly transferred to the next continuous treatment operation.

More specifically, first, steam is supplied to the reboiler 67 of the first distillation column 1 to operate the boiling mechanism and thereby initiate heating of the first distillation column. The flow rate of the steam is gradually increased up to a set value, for example, over about 40 min. Thereafter, the temperature of the lower packing layer is detected by the thermometer 51 to conduct a cascade control for maintaining the lower packing layer, for example, in a temperature range of 130 to 140° C. By detecting the temperature of the lower packing layer (recovery portion) to perform a cascade control for the flow rate of steam through the reboiler 67, it is possible to conduct optimum heating of the first distillation column 1 corresponding to the variation in amount of the raw NMP fed thereto and the variation in concentration of the raw NMP, i.e., the variation in water content in the raw NMP.

Meanwhile, in the lower packing layer (recovery portion) of the first distillation column 1, the difference in boiling point between NMP and water becomes large, so that there is present a large temperature gradient. In the case where such a position is selected as the detecting position of the thermometer 51, the variation in temperature of the lower packing layer and the variation in flow rate of steam both become large owing to an excessively high response rate. In consequence, the temperature detecting position (mounting position) of the thermometer 51 is set to the position where the temperature of the NMP component having a somewhat low response rate is detected, so that the above variation can be reduced. As a result, the operation of the distillation apparatus can be performed even in response to considerably large change in composition of the raw NMP, and further both of the concentration of water in NMP in the bottom portion and the concentration of NMP in water in the top portion can be reduced, resulting in enhanced separation efficiency. That is, in the present invention, when the circulation operation (total reflux operation) is performed to keep the respective distillation columns in a stationary state, the flow rate of steam through the reboiler in the first distillation column 1 may be controlled such that the temperature of the recovery portion is equal to a temperature corresponding to the boiling point of NMP.

Next, steam is supplied to the reboiler 68 of the second distillation column 2, and the boiling mechanism is operated to initiate heating of the second distillation column. The flow rate of steam supplied is gradually increased over about 40 min until reaching the flow rate as designed. Thereafter, the temperature of the lower packing layer is detected by the thermometer 53 to maintain the bottom portion of the second distillation column 2 and the lower packing layer, for example, in a temperature rang of 100 to 130° C. and also maintain an upper packing layer in a temperature rang of 100 to 130° C.

Successively, while operating the first distillation column 1 and the second distillation column 2, the circulation operation in which the raw NMP is continuously fed thereto and the bottoms of the first distillation column 1 and the second distillation column 2 are fed back to the raw material tank 41 is performed, thereby finely adjusting values of preset data for the automatic operation. As a result, it is possible to control operating conditions within the system to optimum ones.

More specifically, first, continuous feed of the raw NMP is initiated. Upon feeding the raw NMP, the opening degree of the flow control valve 74 is gradually increased, for example, the flow rate as designed is reached over 90 min, so as not to cause turbulence of the operation owing to rapid feed to the first distillation column 1. On the other hand, continuous discharge of the distillate from the first distillation column 1 is initiated. At this time, the opening degree of the flow control valve 75 is gradually increased so as to reach a predetermined flow rate over about 15 min, so that turbulence of the operation within the first distillation column owing to rapid variation in reflux ratio therethrough can be prevented. The reflux ratio of the first distillation column 1 is distributed with the predetermined ratio by a reflux distribution mechanism. The distillate from the first distillation column 1 is fed back to the raw material tank 41 through the flow path 100. Also, discharge of the bottoms from the first distillation column 1 is initiated. At this time, the level of the bottom liquid in first distillation column is detected by a level meter 52 to control an amount of the bottom liquid withdrawn and thereby control a level of the liquid in the bottom portion.

Next, continuous discharge of the distillate from the second distillation column 2 is initiated. At this time, the opening degree of the flow control valve 77 is gradually increased to reach the predetermined flow rate over about 15 min, so that turbulence within the second distillation column owing to rapid change in reflux ratio can be suppressed. The reflux ratio of the second distillation column 2 is distributed with the predetermined ratio by a reflux distribution mechanism. The distillate from the second distillation column 2 is fed back to the raw material tank 41 through the flow path 99 in order to keep the concentration of NMP in the raw material and the concentration distribution within the system constant. In addition, discharge of the bottoms from the second distillation column 2 is initiated. At this time, the flow control valve 78 is subjected to ratio control based on the feed flow rate to the second distillation column 2, and the bottoms in an amount of about 10% of the feed flow rate are withdrawn through the flow path 96 as a waste liquid for suppressing concentration of peroxides therein.

Further, in the second distillation column 2, the amount of steam in the reboiler 68 of the boiling mechanism is adjusted using a level meter (not shown) disposed in the bottom portion thereof to control an amount of the distillate discharged therefrom. With the above control procedure, it is possible to prevent occurrence of such a risk that the distillate out of specification is discharged from the top portion of the second distillation column 2 owing to the variation in feed amount to the second distillation column. As described above, the operation conditions of the distillation apparatus are controlled to optimum conditions by performing the circulation operation. Then, the place to which the distillate from the second distillation column 2 is to be fed is switched from the raw material tank 41, for example, to the first check drum 31, thereby initiating the continuous treatment operation.

More specifically, the distillation apparatus according to the present invention is provided as an automatic treatment function with a start-up function of previously performing a circulation operation in each of the first distillation column 1 and the second distillation column 2 in which the raw NMP in the raw material tank 41 (liquid to be treated) is fed to the first distillation column 1 and the distillate from the second distillation column 2 is fed back to the raw material tank 41 to control the respective distillation columns in a stationary state, and then initiating a continuous treatment operation of the distillation apparatus. With such a start-up function, it is possible to control the system in a stationary state completely adapted to the composition of the raw NMP fed thereto, thereby smoothly transferring to the continuous treatment operation.

[Continuous Treatment Operation]

In the continuous treatment operation, the distillate from the first distillation column 1 (water comprising low-boiling components) is discharged out of the system through a flow path 92, and the bottoms of the first distillation column 1 (high-concentration NMP) are fed to the second distillation column 2 through a flow path 93. In addition, the distillate from the second distillation column 2 (high-purity NMP) is fed to the first check drum 31 and the second check drum 32 through a flow path 95 and temporarily stored therein, and the bottoms of the second distillation column 2 (high-concentration NMP comprising high-boiling components) are fed to a water liquid tank 43 through a flow path 96, a waste liquid cooler 35 and a flow path 97.

The high-purity NMP as the distillate withdrawn from the second distillation column 2 is alternately stored in the first check drum 31 and the second check drum 32 in a switching manner. At this time, the switching between the first check drum 31 and the second check drum 32 is automatically conducted by controlling a changeover valve (not shown) disposed on the flow path 95 between these check drums on the basis of the value detected by a level meter (not shown) disposed in each of the first check drum 31 and the second check drum 32.

For example, when a predetermined amount (for example, an amount corresponding to 80% of a capacity of the container) of the high-purity NMP is stored in the first check drum 31, feeding of the high-purity NMP through the flow path 95 is switched so as to feed the high-purity NMP to the second check drum 32, and a switching valve (not shown) on the flow path 86 is opened, and a product withdrawal pump 62 is actuated to conduct a minimum flow operation such that the concentration of NMP in the first check drum 31 becomes uniform. Then, before the second check drum 32 is fulfilled, the purity of the high-purity NMP (product) in the first check drum 31 is analyzed. When the purity of the high-purity NMP meet the standard as required, the high-purity NMP is delivered to the product tank 42 through the flow path 88. Similarly, when a predetermined amount of the high-purity NMP is stored in the second check drum 32, the switching of feed of the high-purity NMP through the flow path 95 is conducted, and a switching valve (not shown) on the flow path 87 is opened, and the product withdrawal pump 62 is actuated to conduct a minimum flow operation such that the concentration of NMP in the second check drum 32 becomes uniform. Then, before the first check drum 31 is fulfilled, the purity of the high-purity NMP (product) in the second check drum 32 is analyzed. When the purity of the high-purity NMP meet the standard as required, the high-purity NMP is delivered to the product tank 42.

Meanwhile, the purity of the high-purity NMP is analyzed by sampling a part of the high-purity NMP from the respective check drums 31 and 32 through a sampling flow path (not shown) and subjecting the thus sampled NMP to gas chromatography. As a simple analyzing method, there may also be used the method of calculating the NMP purity from a water concentration therein as measured using a Karl-Fischer moisture meter. Further, in the case where the purity of the NMP does not reach the predetermined standard, the NMP stored in the respective check drums 31 and 32 is returned to the raw material tank 41 through the flow path 99. On the other hand, the waste liquid (high-concentration NMP comprising high-boiling components) stored in the waste liquid tank 43 is appropriately discharged to drums or a lorry car out of the system through a waste liquid discharge pump 64 and a flow path 98.

[Switching of Operation]

In the continuous treatment operation, there may also occur such a case in which the throughput or water content in the raw NMP vary depending upon the variation in process for production of electrodes, so that the amount of the raw NMP stored in the raw material tank 41 or the amount of the product stored in the product tank 42 (amount of the high-purity NMP stored) also vary. In consequence, when the amount of the raw NMP stored in the raw material tank 41 is reduced during the continuous treatment operation or when the amount of the high-purity NMP stored in the product tank 42 is increased during the continuous treatment operation, the operation of the distillation apparatus is not stopped but kept in a stand-by state, and transferred again to the above circulation operation.

More specifically, the distillation apparatus according to the present invention is also provided as an automatic treatment function with an operational mode switching function in which upon the continuous treatment operation, an operational mode of the distillation apparatus is switched again to the circulation operation in the case where a level of the liquid in the raw material tank 41 is lowered up to a predetermined height during the continuous treatment operation or in the case where a level of the liquid product in the product tank 42 is raised up to a predetermined height during the continuous treatment operation. The level of the liquid in the raw material tank 41 (lower height) is preset, for example, to a height corresponding to 20% of a capacity of the raw material tank, and the level of the liquid product in the product tank 42 (upper height) is preset, for example, to a height corresponding to 90% of a capacity of the product tank.

Further, the operational mode switching function may be conducted such that the operation is switched by detecting a level of the liquid in each of the first check drum 31 and the second check drum 32. That is, in the preferred embodiment, not only in the case where a level of the liquid in the raw material tank 41 is lowered up to a predetermined height during the continuous treatment operation or in the case where a level of the liquid product in the product tank 42 is raised up to a predetermined height during the continuous treatment operation as described above, but also in the case where a level of the liquid in the first check drum 31 or the second check drum 32 is raised up to a predetermined height during the continuous treatment operation, the operation is switched again to the circulation operation.

Thus, after transferring to the circulation operation during the continuous treatment operation, the operation conditions of the first distillation column 1 and the second distillation column 2 can be automatically adjusted as described above. Then, it is judged whether or not the level of the liquid in each of the raw material tank 41, the product tank 42, the first check drum 31 and the second check drum 32 fall within an allowable range. When the liquid level lies within the allowable range, the operation of the distillation apparatus is transferred again to the automatic continuous treatment operation. In the present invention, with the above operational mode switching function, it is possible to operate the distillation apparatus in a suitable manner adaptable to the variation in throughput of the raw material NMP and the variation in water content in the raw material NMP, and obtain purified high-purity NMP in a safe and stable manner.

[Stopping of Operation]

During the continuous treatment operation as described above, when the manipulation for stopping the operation is made on a control panel or when an interlock mechanism is actuated owing to detection of any failure (in the case of emergent stopping), the operation of the distillation apparatus is automatically stopped according to the following procedure based on a preset program. That is, upon stopping an operation of the distillation apparatus, first, the feeding of steam to the reboiler 67 of the boiling mechanism in the first distillation column 1 is stopped, and the feeding of steam to the reboiler 68 of the boiling mechanism in the second distillation column 2 is also stopped, whereby the withdrawal of each of the distillate and bottoms in the first distillation column 1 and the second distillation column 2 is stopped. Next, after stopping all pumps including the raw material feed pump 61, the product withdrawal pump 62 and the vacuum pump 34, a vacuum breaking operation is carried out. That is, an inside pressure of the system is increased until reaching approximately an atmospheric pressure.

More specifically, the distillation apparatus according to the present invention is provided, as an automatic treatment function, with an automatic stopping function in which in response to the manipulation for stopping the operation or the emergent stopping manipulation, the operation of the reboiler in each of the first and second distillation columns, the feeding of the liquid to be treated from the raw material tank, and the withdrawal of the distillate and bottoms from each of the first and second distillation columns, are stopped, and an inert gas is fed to the first and second distillation columns to thereby equalize the pressure within the respective distillation columns. In the present invention, with the provision of the above automatic stopping function, it is possible to held the composition of the liquid within each of the first and second distillation columns in the same state as upon stopping the operation, and more smoothly restart the operation without turbulence of the composition of the liquid being present within the respective distillation columns.

As described above, the distillation apparatus according to the present invention comprises the first distillation column in which water comprising low-boiling components is removed to obtain purified high-concentration NMP, and the second distillation column in which high-boiling components are removed from the high-concentration NMP to purify the high-concentration NMP and obtain high-purity NMP, and further is provided, an automatic treatment function, with a start-up function in which a reduced pressure operation and a circulation operation are successively performed in the first and second distillation columns 1 and 2 to control the respective distillation columns in a stationary state, and then a continuous treatment operation of the distillation apparatus is initiated; and an operational mode switching function in which upon the continuous treatment operation, the level of the liquid in each of the raw material tank 41 and the product tank 42 is detected, and the operation of the distillation apparatus is switched to the circulation operation according to the variation in amount of the raw NMP fed or the water content in the raw NMP. Therefore, without need of highly skilled techniques, it is possible to purify NMP on-site in a simple and safe manner by automatically operating the distillation apparatus. Meanwhile, in the distillation apparatus according to the present invention, the raw material tank 41, the product tank 42, the waste liquid tank 43 and equipments attached thereto may be conventionally known ones except for the first distillation column 1, the second distillation column 2 and equipments attached thereto which are disposed within the frame shown by a chain line in FIG. 1.

EXPLANATION OF REFERENCE NUMERALS

1: First distillation column; 2: Second distillation column; 31: First check drum; 32: Second check drum; 34: Vacuum pump; 41: Raw material tank; 42: Product tank; 43: Waste liquid tank; 51: Thermometer; 52: Level meter; 53: Thermometer; 61: Raw material feed pump; 62: Product withdrawal pump; 67: Reboiler; 68: Reboiler; 71 to 73: Pressure regulating valves; 74 to 78: Flow control valves; 76: Discharge valve; 80 to 98: Flow paths

The invention claimed is:
1. A method of purifying a spent N-methyl-2-pyrrolidone comprising low-boiling components and high-boiling components, the method comprising the steps of:
   recovering a spent N-methyl-2-pyrrolidone, the spent N-methyl-2-pyrrolidone being mixed with water, and the spent N-methyl-2-pyrrolidone being a spent solvent used in producing an electrode for a lithium ion secondary battery;
   transferring the spent N-methyl-2-pyrrolidone to a raw material tank and transferring the spent N-methyl-2-pyrrolidone from the raw material tank to a first distillation column;
   separating, in the first distillation column, the spent N-methyl-2-pyrrolidone into a first bottoms and a first distillate, the first bottoms comprising a high-concentration N-methyl-2-pyrrolidone comprising not less than 99% by weight N-methyl-2-pyrrolidone, the first distillate having a concentration of water that is higher than a concentration of water in the first bottoms, the first distillate having a first distillate boiling point, the first bottoms having a first bottoms boiling point, the first distillate boiling point being lower than the first bottoms boiling point;
   transferring the first bottoms from the first distillation column to a second distillation column;
   separating, in the second distillation column, the first bottoms into a second bottoms and a second distillate, the second distillate comprising a high-purity N-methyl-2-pyrrolidone comprising not less than 99.9% by weight N-methyl-2-pyrrolidone, the second bottoms having a concentration of N-methyl-2-pyrrolidone that is lower than a concentration of N-methyl-2-pyrrolidone in the second distillate;
   transferring the second distillate to a product tank or a check drum for storing the high-purity N-methyl-2-pyrrolidone;
   detecting an amount of second distillate in the product tank or check drum;
   detecting an amount of spent N-methyl-2-pyrrolidone in the raw material tank;
   in a first mode,
   recirculating the first distillate from the first distillation column and mixing the first distillate with the spent N-methyl-2-pyrrolidone before transferring the spent N-methyl-2-pyrrolidone to the first distillation column, and
   recirculating the second distillate from the second distillation column and mixing the second distillate with the spent N-methyl-2-pyrrolidone before transferring the spent N-methyl-2-pyrrolidone to the first distillation column;
   in a second mode,
   transferring the second distillate from the second distillation column to a product tank for storing the high-purity N-methyl-2-pyrrolidone,
   removing the second distillate from the product tank,
   transferring the second bottoms to a waste liquid tank, and removing the second bottoms from the waste liquid tank;
   switching from the second mode and to the first mode (i) if the amount of second distillate in the product tank or check drum is larger than a first predetermined amount of second distillate in the product tank or check drum or (ii) if the amount of spent N-methyl-2-pyrrolidone in the raw material tank is smaller than a second predetermined amount of spent N-methyl-2-pyrrolidone in the raw material tank; and
   switching from the first mode to the second mode (i) if the amount of second distillate in the product tank or check drum is smaller than the first predetermined amount of second distillate in the product tank or check drum and (ii) if the amount of spent N-methyl-2-pyrrolidone in the raw material tank is larger than the second predetermined amount of spent N-methyl-2-pyrrolidone in the raw material tank.

2. The method of claim 1, wherein the spent N-methyl-2-pyrrolidone has a concentration of N-methyl-2-pyrrolidone of more than 80% by weight.

3. The method of claim 1, further comprising
   in a third mode conducted before the first mode,
   reducing a pressure of the first distillation column and reducing a pressure of the second distillation column.

4. The method of claim 1, wherein the first mode is a start-up circulation operation, and the second mode is a continuous treatment operation.

5. The method of claim 1, wherein the second predetermined amount is 20% of a volume capacity of the raw material tank.

6. The method of claim 1, wherein the first predetermined amount is 90% of a volume capacity of the product tank.

7. The method of claim 1, further comprising transferring the second distillate from the check drum if an amount of high-purity N-methyl-2-pyrrolidone exceeds a third predetermined amount of the high-purity N-methyl-2-pyrrolidone.

8. The method of claim 7, wherein the third predetermined amount is 80% of a volume capacity of the check drum.

9. The method of claim 1, further comprising feeding steam through a reboiler according to a flowrate of spent N-methyl-2-pyrrolidone transferred to the first distillation, wherein a portion of the first bottoms is recirculated to the first distillation column after passing through the reboiler.

10. The method of claim 1, further comprising feeding steam through a reboiler such that a temperature of a lower packing layer of the first distillation column is adjusted to a temperature corresponding to a boiling point of N-methyl- 2-pyrrolidone, wherein a portion of the first bottoms is recirculated to the first distillation column after passing through the reboiler.

11. The method of claim 1, further comprising
in a fourth mode,
stopping a first reboiler of the first distillation column and a second reboiler of the second distillation column,
stopping the first distillation column and second distillation column,
stopping transferring spent N-methyl-2-pyrrolidone to the first distillation column,
stopping removing the first distillate and the first bottoms from the first distillation column,
stopping removing the second distillate and the second bottoms from the second distillation column, and
feeding an inert gas to the first distillation column and the second distillation column to equalize a pressure within the first and second distillation columns.

* * * * *